United States Patent [19]
Lang et al.

[11] Patent Number: 6,071,953
[45] Date of Patent: Jun. 6, 2000

[54] SULFONAMIDE-SUBSTITUTED CHROMANS, PROCESSES FOR THEIR PREPARATION, THEIR USE AS MEDICAMENT OR DIAGNOSTIC AID, AND MEDICAMENT COMPRISING THEM

[75] Inventors: Hans Jochen Lang, Hofheim; Joachim Brendel, Bad Vilbel; Uwe Gerlach, Hattersheim; Klaus Weidmann, Kronberg, all of Germany

[73] Assignee: Hoechst Aktiengesellschaft, Frankfurt am Main, Germany

[21] Appl. No.: 09/026,513

[22] Filed: Feb. 19, 1998

[30] Foreign Application Priority Data

Feb. 20, 1997 [DE] Germany ............ 197 06 675

[51] Int. Cl.[7] .......... A01N 43/16; C07D 311/74; C07D 311/76
[52] U.S. Cl. .......... 514/457; 514/821; 514/867; 514/925; 514/926; 549/399; 549/404
[58] Field of Search .......... 549/399, 404; 514/457, 821, 867, 925, 926

[56] References Cited

FOREIGN PATENT DOCUMENTS

| 0 370 901 | 5/1990 | European Pat. Off. |
| 0 389 861 | 10/1990 | European Pat. Off. |
| 88/061195 | 8/1988 | WIPO .................... 549/404 |

OTHER PUBLICATIONS

Wargh et al, Chemical Abstract vol. 125 No. 191888, "The cAMP–Regulated & 293 B–Inhibited K+ Conductance of Rat Colonic Crypt Base Cells." 1996.

Lohrmann et al, Chemical Abstract vol. 123 No. 160095, "A New Class of Inhibitors of cAMP–Mediated Cl–Secretion in Rabbit Colon." 1995.

R. M. Soll et al.; "N–Sulfonamides of Benzopyran–Related Potassium Channel Openers: Conversion of Glyburide Insensitive Smooth Muscle Relaxants to Potent Smooth Muscle Contractors", Bioorganic & Medicinal Chemistry Letters, vol. 4, No. 5, pp. 769–773, (1994).

Chemical Abstract vol. 123 No. 132796, Ecke et al, "A Chromanol Type of K+ Channel Blocker Inhibits Forskolin." 1995.

*Primary Examiner*—John Kight
*Assistant Examiner*—Raymond Covington
*Attorney, Agent, or Firm*—Finnegan, Henderson, Farabow, Garrett & Dunner, L.L.P.

[57] ABSTRACT

Chromans of formula I

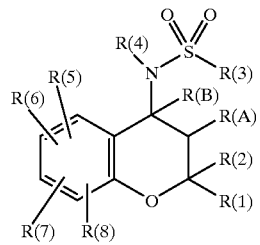

with the meanings of R(A), R(B) and R(1) to R(8) stated in the specification are suitable for producing a medicament for blocking the $K^+$ channel that is opened by cyclic adenosine monophosphate (cAMP); also for producing medicaments for inhibiting gastric acid secretion; for the treatment of ulcers of the stomach and the intestinal region, in particular the duodenum, for the treatment of reflux esophagitis, for the treatment of diarrheal disorders, for the treatment and prevention of all types of arrhythmias, including atrial, ventricular and supraventricular arrhythmias, for controlling reentry arrhythmias and for preventing sudden heart death as a result of ventricular fibrillation.

16 Claims, No Drawings

SULFONAMIDE-SUBSTITUTED CHROMANS, PROCESSES FOR THEIR PREPARATION, THEIR USE AS MEDICAMENT OR DIAGNOSTIC AID, AND MEDICAMENT COMPRISING THEM

FIELD OF THE INVENTION

The invention relates to chromans of formula I

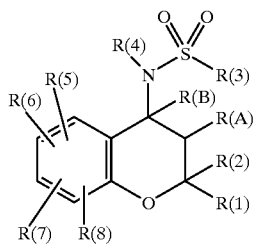

I in which:

R(1) and R(2)
 are, independently of one another, hydrogen, $CF_3$, $C_2F_5$, $C_3F_7$, alkyl having 1, 2, 3, 4, 5 or 6 carbon atoms or phenyl,
  which is unsubstituted or substituted by 1 or 2 substituents selected from the group consisting of F, Cl, Br, I, $CF_3$, methyl, methoxy, sulfamoyl and methylsulfonyl;
or
R(1) and R(2)
 together are an alkylene chain having 2, 3, 4, 5, 6, 7, 8, 9 or 10 carbon atoms;
R(A) is hydroxyl, alkanoyloxy having 1, 2, 3, 4, 5 or 6 carbon atoms or alkylsulfonyloxy having 1, 2, 3, 4, 5 or 6 carbon atoms;
R(B) is hydrogen;
or
R(A) and R(B)
 together are a bond;
R(3) is R(9)—$C_nH_{2n}$(NR(11))$_m$—;
 R(9) is hydrogen or cycloalkyl having 3, 4, 5, 6, 7 or 8 carbon atoms;
 n is zero, 1, 2, 3, 4, 5, 6, 7, 8, 9 or 10;
 m is zero or 1;
 R(11) is hydrogen or alkyl having 1, 2, 3, 4, 5 or 6 carbon atoms;
or
R(11) and R(9)
 together are an alkylene group having 1, 2, 3, 4, 5, 6, 7 or 8 carbon atoms;
 it being possible for one $CH_2$ group in the $C_nH_{2n}$ group to be replaced by —O—, —$SO_{zero, 1\ or\ 2}$— or —NR(10)—;
R(10) is hydrogen, methyl or ethyl;
R(4) is R(12)—$C_rH_{2r}$;
 R(12) is hydrogen, cycloalkyl having 3, 4, 5, 6, 7 or 8 carbon atoms, piperidyl, 1-pyrrolidinyl, N-morpholino, N-methylpiperazino, $CF_3$, $C_2F_5$, $C_3F_7$, pyridyl, thienyl, imidazolyl or phenyl,
  where pyridyl, thienyl, imidazolyl or phenyl are unsubstituted or substituted by 1 or 2 substituents selected from the group consisting of F, Cl, Br, I, $CF_3$, methyl, methoxy, sulfamoyl, methylsulfonyl and methylsulfonylamino;

r is zero, 1, 2, 3, 4, 5, 6, 7, 8, 9, 10, 11, 12, 13, 14, 15, 16, 17, 18, 19 or 20;
 it being possible for one $CH_2$ group in the $C_rH_{2r}$ group to be replaced by —O—, —CH=CH—, —C≡C—, —CO—, —CO—O—, —$SO_{zero, 1\ or\ 2}$— or —NR(10)—;
R(5), R(6), R(7) and R(8)
 are, independently of one another, hydrogen, F, Cl, Br, I, alkyl having 1, 2, 3, 4, 5 or 6 carbon atoms, cycloalkyl having 3, 4, 5, 6, 7 or 8 carbon atoms, —CN, —$CF_3$, —$C_2F_5$, —$C_3F_7$, —$N_3$, —$NO_2$, —CONR(13)R(14), —COOR(15), R(16)—$C_sH_{2s}$—Y— or phenyl,
  which is unsubstituted or substituted by 1 or 2 substituents selected from the group consisting of F, Cl, Br, I, $CF_3$, methyl, methoxy, sulfamoyl and methylsulfonyl;
R(13) and R(14)
 are, independently of one another, hydrogen or alkyl having 1, 2 or 3 carbon atoms;
R(15) is hydrogen, methyl, ethyl, phenyl or —$C_uH_{2u}$—NR(13)R(14);
 u is 2 or 3;
R(16) is hydrogen, cycloalkyl having 3, 4, 5, 6, 7 or 8 carbon atoms, —COOR(15), thienyl, imidazolyl, pyridyl, quinolyl, isoquinolyl, piperidyl, 1-pyrrolidinyl, N-morpholino, N-methylpiperazino, $CF_3$, $C_2F_5$, $C_3F_7$ or phenyl,
  which is unsubstituted or substituted by 1 or 2 substituents selected from the group consisting of F, Cl, Br, I, $CF_3$, methyl, methoxy, sulfamoyl and methylsulfonyl;
 s is zero, 1, 2, 3, 4, 5 or 6;
 Y is —S—, —SO—, —$SO_2$—, —CO—, —$SO_2$—NR(10)—, —O—, —NR(10)— or —CO—NR(10);
but with the condition that two of the substituents R(5), R(6), R(7) and R(8) are not hydrogen; or physiologically tolerated salts thereof.

Preference is given to compounds of formula I in which:
R(1) and R(2)
 are, independently of one another, hydrogen, alkyl having 1, 2 or 3 carbon atoms or phenyl,
  which is unsubstituted or substituted by 1 or 2 substituents selected from the group consisting of F, Cl, Br, I, $CF_3$, methyl, methoxy, sulfamoyl and methylsulfonyl;
or
R(1) and R(2)
 together are an alkylene chain having 4 or 5 carbon atoms;
R(A) is hydroxyl or acetoxy;
R(B) is hydrogen;
or
R(A) and R(B)
 together are a bond;
R(3) is R(9)—$C_nH_{2n}$(NR(11))$_m$—;
 R(9) is hydrogen;
 n is zero, 1, 2, 3, 4, 5 or 6;
 m is zero or 1;
 R(11) is hydrogen or alkyl having 1, 2, 3 or 4 carbon atoms;
R(10) is hydrogen, methyl or ethyl;
R(4) is R(12)—$C_rH_{2r}$;
 R(12) is hydrogen, cycloalkyl having 3, 4, 5, 6, 7 or 8 carbon atoms, $CF_3$, pyridyl or phenyl,
  where pyridyl and phenyl are unsubstituted or substituted by 1 or 2 substituents selected from the group consisting of F, Cl, $CF_3$, sulfamoyl and methylsulfonyl;

r is zero, 1, 2, 3, 4, 5, 6, 7, 8, 9 or 10;

it being possible for one $CH_2$ group in the $C_rH_{2r}$ group to be replaced by —O—, —CO—, —CO—O—, —$SO_{zero, 1\ or\ 2}$—;

R(5), R(6), R(7) and R(8)

are, independently of one another, hydrogen, F, Cl, Br, alkyl having 1, 2, 3 or 4 carbon atoms, —CN, —$CF_3$, —$NO_2$, —CONR(13)R(14), —COOR(15), R(16)—$C_sH_{2s}$—Y— or phenyl, which is unsubstituted or substituted by 1 or 2 substituents selected from the group consisting of F, Cl, and $CF_3$;

R(13) and R(14)

are, independently of one another, hydrogen or alkyl having 1, 2 or 3 carbon atoms;

R(15) is methyl, ethyl, phenyl or —$C_uH_{2u}$—NR(13)R(14);

u is 2 or 3;

R(16) is hydrogen, cycloalkyl having 5 or 6 carbon atoms, $CF_3$, $C_2F_5$, $C_3F_7$ or phenyl, which is unsubstituted or substituted by 1 or 2 substituents selected from the group consisting of F, Cl, Br, $CF_3$, methyl, methoxy, sulfamoyl and methylsulfonyl;

s is zero, 1, 2, 3 or 4;

Y is —S—, —SO—, —$SO_2$—, —CO—, —$SO_2$—NR(10)—, —O—, —NR(10)— or —CO—NR(10);

but with the condition that two of the substituents R(5), R(6), R(7) and R(8) are not hydrogen; or physiologically tolerated salts thereof.

Particular preference is given to compounds of formula I in which:

R(1) and R(2)

are, independently of one another, alkyl having 1, 2 or 3 carbon atoms;

or

R(1) and R(2)

together are an alkylene chain having 4 or 5 carbon atoms;

R(A) is hydroxyl;

R(B) is hydrogen;

or

R(A) and R(B)

together are a bond;

R(3) is alkyl having 1, 2 or 3 carbon atoms, dimethylamino or diethylamino;

R(4) is R(12)—$C_rH_{2r}$;

R(12) is hydrogen, cycloalkyl having 5 or 6 carbon atoms or $CF_3$;

r is zero, 1, 2, 3, 4, 5, 6, 7 or 8;

it being possible for one $CH_2$ group in the $C_rH_{2r}$ group to be replaced by —O—, —CO—, —CO—O—, —$SO_{zero, 1\ or\ 2}$—;

R(5), R(6), R(7) and R(8)

are, independently of one another, hydrogen, F, Cl, Br, alkyl having 1 or 2 carbon atoms, —CN, —$NO_2$, —COOR(15), R(16)—$C_sH_{2s}$—Y— or phenyl, which is unsubstituted or substituted by 1 or 2 substituents selected from the group consisting of F and Cl;

R(15) is methyl, ethyl, phenyl or —$C_uH_{2u}$—NR(13)R(14);

u is 2 or 3;

R(13) and R(14)

are, independently of one another, hydrogen or alkyl having 1, 2 or 3 carbon atoms;

R(16) is hydrogen, $CF_3$ or phenyl, s is zero, 1, 2, 3 or 4;

Y is —S—, —SO—, —$SO_2$—, —CO—, —$SO_2$—NR(10)—, —O—, —NR(10)— or —CO—NR(10);

R(10) is hydrogen or methyl;

but with the condition that two of the substituents R(5), R(6), R(7) and R(8) are not hydrogen; or physiologically tolerated salts thereof.

If the compounds of formula I contain an acidic or basic group or a basic heterocycle, the invention also relates to the corresponding pharmacologically and toxicologically acceptable salts. Thus, the compounds of formula I that have one or more —COOH groups can be used for example as alkali metal salts, preferably as sodium or potassium salts. Compounds of formula I that have a basic group that can be protonated or a basic heterocyclic radical can also be used in the form of their organic or inorganic pharmacologically and toxicologically acceptable acid addition salts, for example as hydrochlorides, methanesulfonates, acetates, lactates, maleates, fumarates, malates, gluconates etc. If the compounds of formula I contain an acidic and basic group in the same molecule, the invention also includes, besides the salt forms described, internal salts, called betaines.

If the substituents of the compound of formula I contain groups with different stereochemical possibilities, the invention also includes the individual possible stereoisomers. Thus, the compounds of formula I contain chiral centers in position 3 and 4 of the chroman system so that the individual pure optical isomers and any mixtures of the optically isomeric substances form part of the invention.

The compounds of formula I can be prepared by various chemical processes, which likewise form part of the invention.

Thus, a compound of formula I is obtained by a) reacting, in a manner known per se, a compound of formula II:

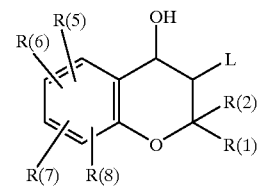

II in which R(1), R(2), R(5), R(6), R(7) and R(8) have the stated meaning, and L is the nucleofugic leaving group customary for an alkylation, in particular Cl, Br or I, with a sulfonamide or its salt of formula III:

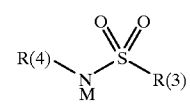

III in which R(3) and R(4) have the stated meaning, and M is hydrogen or a metal atom, particularly preferably lithium, sodium or potassium;

or by b) reacting, in a manner known per se, an epoxide of formula IV:

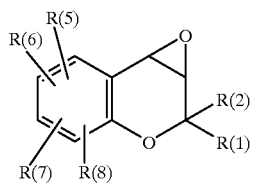

IV in which R(1), R(2), R(5), R(6), R(7) and R(8) have the stated meaning, with a sulfonamide or its salt of formula III

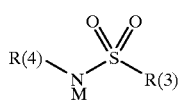

III in which R(3) and R(4) have the stated meaning, and M is hydrogen or a metal atom, particularly preferably lithium, sodium or potassium;

or by c) reacting a compound of formula V:

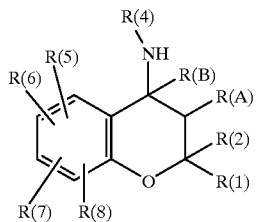

V in which R(1), R(2), R(4), R(5), R(6), R(7), R(8), R(A) have the stated meaning, and R(B) and R(A) equal OH and R(B) equals hydrogen, with a sulfonic acid derivative of formula VI

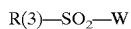

R(3)—SO₂—W    VI in which R(3) has the stated meaning, and W is a nucleofugic leaving group such as fluorine, bromine, 1-imidazolyl, but especially chlorine;

or by d) reacting, in the manner of an alkylation reaction, a compound of formula VII:

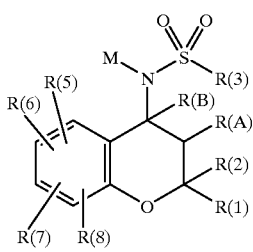

VII in which R(1), R(2), R(3), R(5), R(6), R(7), R(8), R(A), R(B) and M have the stated meaning, in a manner known per se with an alkylating agent of formula VIII

R(4)—L    VIII in which R(4) has the stated meaning, with the exception of hydrogen, and L has the stated meaning;

or by e) carrying out in a compound of formula I:

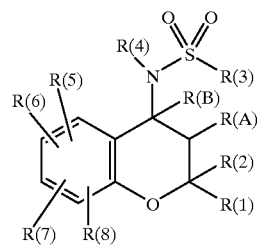

I in which R(10) to R(4) have the stated meaning, an aromatic substitution reaction in at least one position R(5) to R(8);

or by f) converting compounds of formula I in which R(1) to R(8) and R(A) have the stated meaning, and R(B) is hydrogen, by elimination of R(A) and R(B) into chromenes of the general formula I in which R(A) and R(B) are a bond, and the remaining substituents have the stated meaning.

Procedure a)

describes the alkylation, known per se, of a sulfonamide or of one of its salts of formula III by a chroman derivative of formula II having an alkylating action. Since the alkylation of a sulfonamide takes place starting from the salt form, on use of a free sulfonamide (formula III, M=H) it is necessary to generate, by the action of a base, a sulfonamide salt (formula III, M=cation) that is distinguished by greater nucleophilicity and thus higher reactivity. If free sulfonamide (M=H) is employed, the sulfonamide is deprotonated to give the salt in situ preferably with use of bases, which themselves have only little, or no, alkylating action, such as sodium carbonate, potassium carbonate, a highly sterically hindered amine, for example dicyclohexylamine, N,N,N-dicyclohexylethylamine or other strong nitrogenous bases of low nucleophilicity, for example DBU, N,N',N"-triisopropylguanidine, etc. However, it is also possible to employ other bases customarily used for the reaction, such as potassium tert-butoxide, sodium methoxide, alkali metal hydrogen carbonates, alkali metal hydroxides such as, for example, LiOH, NaOH or KOH, or alkaline earth metal hydroxides, for example Ca(OH)₂.

It is preferable to use for this aprotic polar solvents such as dimethylformamide, dimethylacetamide, tetramethylurea, hexamethylphosphoramide, tetrahydrofuran, etc. However, it is also possible in principle to use polar protic solvents such as water, methanol, ethanol, isopropanol, ethylene glycol or its oligomers and the corresponding (mono)ethers thereof. The reaction is preferably carried out at a temperature in the range from 20 to 140° C., particularly preferably from 40 to 100° C. It is also possible and beneficial for procedure a) to be carried out under the conditions of two-phase catalysis.

The compounds of formula II with L equal to Br are obtained, for example, in a manner known from the literature from a chromene of formula XI:

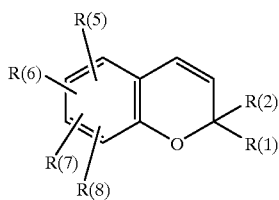

XI with NB5 in the presence of NaOH.

The chromenes of formula XI are obtained in analogy to the literature, for example, by eliminating water from 4-chromanols of formula XII:

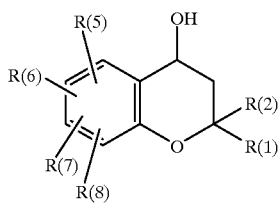

XII by the action of an acid, for example of sulfuric acid or by thermal cyclization, known from the literature, of alkyne ethers of formula XIII:

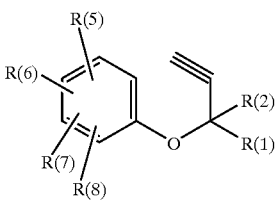

XIII

The 4-chromanols are obtained in a manner known from the literature by reducing the corresponding chromanones XIV;

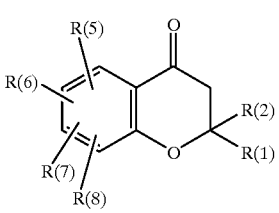

XIV which are obtained in a known reaction from the acetophenone derivatives of formula XV by cyclizing aldol condensation:

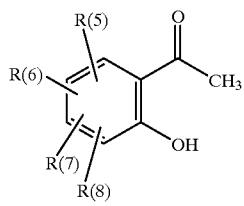

XV with a ketone XVI:

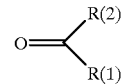

XVI

The compounds of formula III are preferably obtained by reacting the corresponding sulfonyl chloride with an amine. The preparation of sulfonamides is adequately described in the scientific literature and in the patent literature.

Procedure b)

describes the reaction, which is known per se and is frequently used, of an epoxide of formula IV with a sulfonamide of formula III or one of its salts. It has proven particularly beneficial for this purpose to use the free sulfonamide of formula III in the presence of catalytic amounts of one of its salts, for example of the corresponding $Na^+$ salt, which can in turn advantageously be generated in situ in a simple manner known from the literature by adding a small amount of a sufficiently strong base, for example sodium hydride, to a solution or suspension of the sulfonamide. This reaction is advantageously carried out in the solvents described for procedure a) and in the temperature ranges described therefor. The epoxides of formula IV are obtained in a manner known from the literature from the corresponding 3,4-dehydrochromans by epoxidation or by elimination of HL from compounds of formula II with bases.

Procedure c)

describes the reaction, which is known per se and frequently used, of an activated sulfonyl compound of formula VI, in particular of a chlorosulfonyl compound (W=Cl), with an amine of formula V to give the corresponding sulfonamide derivative of formula I. The reaction can in principle be carried out without solvent, but reactions of this type are in most cases carried out using a solvent.

The reaction preferably takes place using a polar solvent, preferably in the presence of a base, which can itself be used as solvent, for example on use of triethylamine, pyridine and its homologs. Examples of solvents that are preferably used include water, aliphatic alcohols, for example methanol, ethanol, isopropanol, sec-butyl, ethylene glycol and its monomeric and oligomeric monoalkyl and dialkyl ethers, tetrahydrofuran, dioxane, dialkylated amides such as DMF, DMA, and TMU and HMPT. The temperature used for this is from 0 to 160° C., preferably from 20 to 100° C.

The amines of formula V are obtained in a manner known per se from the literature, preferably from the corresponding compounds of formula II or the epoxides of formula IV by reacting them either with ammonia or with an amine of formula IX

R(4)—NH$_2$    IX with R(4) having the stated meaning.

Procedure d)

describes, just like procedure a), the alkylation reaction known per se of a sulfonamide or of one of its salts VII with an alkylating agent of formula VIII. In accordance with this analogy of the reactions, the reaction conditions already described in detail for procedure a) apply to procedure d).

The preparation of the sulfonamide derivatives VII and their precursors has already been described for procedure c). The alkylating agents VII are prepared by analogous methods from the literature or as described for procedure a), preferably from the corresponding hydroxy compounds (formula VII with L equal to —OH).

Procedure e)

describes the further chemical transformation of compounds of formula I according to the invention into other compounds of formula I, for example by electrophilic substitution reactions in one or more of the positions identified by R(5) to R(8). In the case where one or two substituents of the radicals R(5) to R(8) are hydrogen, it is possible to carry out in a preferred manner known from the literature an electrophilic aromatic substitution reaction.

Preferred electrophilic substitution reactions are

1. Aromatic nitration to introduce one or more nitro groups, and subsequent reduction thereof to $NH_2$—,
2. Aromatic halogenation, in particular to introduce chlorine, bromine, iodine,
3. Chlorosulfonation to introduce a chlorosulfonyl group by the action of chlorosulfonic acid,
4. Friedel-Crafts acylation reaction to introduce an acyl radical R(16)—$C_sH_{2s}$—CO— or a sulfonyl radical R(16)—$C_sH_{2s}$—$SO_2$— by the action of the corresponding acid chlorides R(16)—$C_sH_{2s}$—CO—Cl or R(16)—$C_sH_{2s}$—$SO_2$—Cl in the presence of a Lewis acid as Friedel-Crafts catalyst, preferably of anhydrous aluminum chloride.

It is additionally possible with the aid of palladium organic syntheses in a manner known from the literature to introduce numerous groups, for example by replacement of aromatically bonded bromide in one of the substituents R(5), R(6), R(7) or R(8), such as, for example, alkynyl, alkenyl, alkyl, anilino, phenoxy radicals etc.

Procedure f)

describes the conversion of a chromanol of formula I with R(A) equal to OH into a chromene of formula I in which R(A) and R(B) form a bond together. This can be done by eliminating water from the chromanol either directly in the presence of an acid or a base, or after activation of the hydroxyl group R(A), for example by acylation with an alkanoic anhydride having 3–12 carbon atoms.

It is possible in this way also to prepare the compounds of formula I according to the invention in which R(1) to R(5) have the stated meaning, R(B) is hydrogen and R(A) is an alkanoyl radical having 1 to 6 carbon atoms. Subsequent elimination to give the chromene type of formula I in which R(A) and R(B) are a bond together is preferably achieved under base-catalyzed conditions, for example by heating with DBU (diazabicycloundecene).

The compounds of formula I are structurally related to the class of 4-acylamino-chroman derivatives, on which there has been intensive work by pharmaceutical chemists in the last decade, in particular of 2,2-dialkyl-4-acylamino-3-chromanols.

The most prominent representative of such 4-acylaminochromans is cromakalim of formula X:

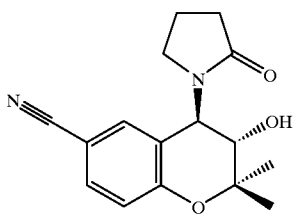

and many follow-up products derived from this product (for example Edwards and Weston, TIPS 11, 417–422 (1990), "Structure Activity Relationships of $K^+$ Channel Openers").

Cromakalim and other related 4-acylaminochroman derivatives are compounds having a relaxant effect on smooth muscular organs so that they are used to lower elevated blood pressure as a result of vascular muscle relaxation and in the treatment of asthma as a result of the relaxation of the smooth muscles of the airways. It is common to all these products that they act at the cellular level, for example of smooth muscle cells, and there lead to opening of certain ATP-sensitive $K^+$ channels. The increase, induced by the escape of $K^+$ ions, in the negative charge in the cell ("hyperpolarization") counteracts, by secondary mechanisms, the increase in intracellular $Ca^{2+}$ and thus cell activation, for example muscle contraction.

In contrast to these 4-acylaminochroman derivatives that, as mentioned, have been identified as openers of the ATP-sensitive $K^+$ channel, the compounds of formula I according to the invention with the 4-sulfonylamino structure surprisingly show a strong and specific blocking (closing) action on a $K^+$ channel that is activated by cyclic adenosine monophosphate (cAMP) and differs fundamentally from the $K^+$(ATP) channel mentioned. Recent investigations show that this $K^+$(cAMP) channel identified in the large bowel is very similar or possibly identical to the $I_{Ks}$ channel identified on the myocardium. As a consequence of this blocking of the $K^+$(cAMP) channel (=$I_{Ks}$ channel), the compounds display pharmacological effects of high therapeutic utility in the living organism.

Thus, the compounds are distinguished as a novel active substance class of potent inhibitors of stimulated gastric acid secretion. The compounds of formula I are thus valuable medicaments for the treatment of ulcers in the stomach and the intestinal region, for example the duodenum. They are likewise suitable, as a consequence of their strong inhibiting effect on the secretion of gastric fluid, as excellent therapeutic agents for treating reflux esophagitis.

The compounds are furthermore distinguished by an antidiarrheal effect and are therefore suitable as pharmaceuticals for treating diarrheal disorders.

The compounds of formula I can furthermore be used as pharmaceuticals for the treatment and prevention of all types of arrhythmias, including atrial, ventricular and supraventricular arrhythmias. They can be used in particular for controlling reentry arrhythmias and for preventing sudden heart death as a result of ventricular fibrillation.

Publications now exist which describe a correlation between an IKS channel-inhibiting effect and the suppression of life-threatening cardiac arrhythmias as induced, for example, by β-adrenergic hyperstimulation (for example T. J. Colatsky, C. H. Follmer and C. F. Starmer; "Channel Specificity in Antiarrhythmic Drug Action; Mechanism of potassium channel block and its role in suppressing and aggravating cardiac arrhythmias", Circulation (1990) 82: 2235–2242; A. E. Busch, K. Malloy, W. J. Groh, M. D. Varnum, J. P. Adelman and J. Maylie; "The Novel Class III Antiarrhythmics NE-10064 and NE-10133 Inhibit $I_{sK}$ Channels in Xenopus Oocytes and $I_{Ks}$ in Guinea Pig Cardiac Myocytes", Biochem. Biophys. Res. Commun. (1994) 202: 265–270).

Besides the abovementioned cromakalim and acylaminochroman derivatives, the literature in recent years has also described compounds which have the 4-sulfonylaminochroman structure and that differ markedly either in the structure or in the biological effect from the compounds of formula I according to the invention. Thus, European published specification 315 009 describes chroman derivatives having a 4-phenylsulfonylamino structure that are distinguished by antithrombotic and antiallergic properties.

European published specification 370 901 describes 3-hydroxychroman derivatives having a 4-phenylsulfonylamino group in which the remaining valency of the nitrogen atom carries a hydrogen atom. These compounds are thus substituted in a different manner in essential groups from formula I or Ia. Correspondingly, these compounds of European published specification 370 901 are found to have effects on the central nervous system, so that they also differ in pharmacological respects.

European published specification 389 861 describes 3-hydroxychroman derivatives with a 4-sulfonylamino group. In this case, the benzopyran derivatives described in the patent are activators or openers of the so-called adenosine triphosphate-sensitive K$^+$ channel (K$^+$(ATP) channel). The pharmacological effects of K$^+$(ATP) channel openers are now well known to be completely different from the $I_{Ks}$ channel blockers described herein. Thus, K$^+$(ATP) channel openers have been shown to have vasodilating and hypotensive properties as are typical of this mechanism. As expected, the K$^+$(ATP) channel openers described and synthesized by the authors show the specific antiarrhythmic properties which are typical for this mechanism of K$^+$channel opening and differ quite fundamentally from the antiarrhythmic properties of the compounds of formula I, especially with regard to the type of arrhythmias to be treated.

It has been impressively shown in a fundamental study by Lucchesi et al. (J. Cardiovasc. Pharmacol. 15 (1990), 452–464) that K$^+$(ATP) channel openers do not have antiarrhythmic effects on the diseased heart undersupplied with oxygen or in the event of sudden ischemias but, on the contrary, actually cause life-threatening profibrillatory effects. These dangerous states are induced as a consequence of the reductions, resulting from the activation of the K$^+$(ATP) channel, in the repolarization time. In contrast to these life-threatening profibrillatory effects on the diseased heart with a deficient supply due to the action of K$^+$(ATP) channel openers, under these conditions, blockers of the K$^+$(cAMP) channel ought to show an antifibrillatory effect. A prominent representative of a structurally related chromanol, which has now appeared in the most recent literature as example of a highly specific $I_{Ks}$ or $I_{sK}$ channel blocker with a corresponding prolongation of the action potential in the heart, is 6-cyano-4-(N-ethylsulfonyl-N-methylamino)-2,2-dimethyl-3-chromanol (Süβbrich et al., Naunyn Schiedebergs Arch. Pharm. (1996) 353 (4. Suppl.), R72; Pflügers Arch.-Eur. J Physiol. 431 (6) (Suppl.), R 22 (1996), A. Busch et al., Pflügers Arch.-Eur. J Physiol. 432 (6) (Suppl.), 1094–1096 (1996)). The invention therefore also relates to the use of compounds of formula I for treating sudden cardiac death, ventricular fibrillation and generally arrhythmias of the diseased heart attributable to the $I_{Ks}$ channel.

The compounds described in the present invention differ from potentially conceivable compounds covered by the claims of EP-A 389 861 and from the chromanols described in the literature ("A New Class of Inhibitors of cAMP-mediated Cl-Secretion in Rabbit Colon, Acting by the Reduction of cAMP-Activated K$^+$ Conductance," Pflügers Arch.-Eur. J Physiol. (1995) 429: 517–530) in that at least two of the substituents of the radicals R(5), R(6), R(7) and R(8) are not hydrogen.

These specific compounds of formula I that were prepared and investigated are distinguished by the superior profile of pharmacological effects such as, for example, by a higher potency and/or by a higher organ selectivity and/or by more favorable pharmacokinetic properties, for example by an extended half-life.

The publication "N-Sulfonamides of Benzopyran-Related Potassium Channel Openers: Conversion of Glyburyde Insensitive Smooth Muscle Relaxants to Potent Smooth Muscle Contractors" in Bioorg. Med. Chem. Lett. (1994) 4:769–773 describes specific trifluoromethyl-substituted 4-sulfonylaminochroman derivatives which, however, in contrast to the K$^+$(cAMP) channel blockers of different structure described herein, have biologically different pharmacological effects and thus other therapeutic indications.

There have also been descriptions in the literature recently of spiro(2H-1-benzopyran-2,4'-piperidines) with an essential basic side group, for example MK-499 "Cardiac Electrophysiology and Antiarrhythmic Actions of Two Long-Acting Spirobenzopyran Piperidine Class III Agents, L-702, 958 and L-706,000 (MK 499)" J Pharmacol. Exp. Ther. (1994) 269:541–554; T. J. Colatsky and T. M. Argentieri, "Potassium Channel Blockers as Antiarrhythmic Drugs"; Drug Develop. Res. (1994) 33:235–249. These "Spirobenzopyran-Piperidines Class III Agents" are, however, very clearly characterized in the literature with regard to their mode of action (P. S. Spector, M. E. Curran, M. T. Keating, M. C. Sanguinetti, Circulation Res. (1996) 78:499–503; J. J. Lynch et al., J. Pharmacol. Exp. Ther. (1994) 269:541–554). In this connection, it is unambiguously described and shown in the cited literature that the antiarrhythmic effect of these compounds is caused by the inhibition of the HERG channel and of the rapidly activating component of the delayed rectifier K$^+$ channel, the $I_{Kr}$ channel. This means that the spirobenzopyran-piperidines are characterized as substances with a proarrhythmic component and with the risk of increased mortality by comparison with placebo, as was shown for this class of active substances in the Sword study. This is in clear contrast with the compounds described herein, whose advantage consists of blocking the slowly activating component of the delayed rectifier K$^+$ channel, the $I_{Ks}$ channel, and which do not have this proarrhythmic component.

Pharmaceuticals which comprise a compound of formula I according to the invention can be administered orally, parenterally, intravenously, rectally or by inhalation, and the preferred administration depends on the particular manifestation of the disease. The compounds of formula I can, moreover, be used alone or together with pharmaceutical ancillary substances, both in veterinary and in human medicine.

The particular ancillary substances suitable for the required pharmaceutical formulation are familiar to the skilled worker on the basis of his expert knowledge. Besides solvents, gels formers, suppository bases, tablet ancillary substances and other active substance carriers, it is possible to use, for example, antioxidants, dispersants, emulsifiers, antifoams, masking flavors, preservatives, solubilizers or dyes.

For a form for oral use, the active compounds are mixed with the additives suitable for this purpose, such as excipients, stabilizers or inert diluents, and converted by conventional methods into the suitable dosage forms such as tablets, coated tablets, hard gelatin capsules, aqueous, alcoholic or oily solutions. Examples of inert carriers that can be used are gum arabic, magnesia, magnesium carbonate, potassium phosphate, lactose, glucose or starch, especially corn starch. Preparation both as dry and as wet granules is also possible. Examples of suitable oily excipients or solvents are vegetable or animal oils, such as sunflower oil or fish liver oil.

For subcutaneous or intravenous administration, the active compounds are converted into a solution, suspension or emulsion, if required with the substances customary for this purpose, such as solubilizers, emulsifiers or other ancillary substances. Examples of suitable solvents are: water, physiological saline or alcohols, for example ethanol, propanol, glycerol, as well as sugar solutions such as glucose or mannitol solutions, or else a mixture of the various solvents mentioned.

Suitable as pharmaceutical formulation for administration in the form of aerosols or sprays are, for example, solutions, suspensions or emulsions of the active substance of formula I in a pharmaceutically acceptable solvent such as, in particular, ethanol or water, or a mixture of such solvents. The formulation may, if required, also contain other pharmaceutical ancillary substances such as surfactants, emulsifiers and stabilizers, and a propellant gas. A composition of this type normally contains the active substance in a concentration of about 0.1 to 10, in particular about 0.3 to 3% by weight.

The dosage of the active substance of formula I to be administered and the frequency of administration depend on the potency and duration of action of the compounds used; but also on the nature and severity of the disease to be treated and on the sex, age, weight and individual responsiveness of the mammal to be treated.

The daily dose of a compound of formula I for a patient weighing about 75 kg is on average at least 0.001 mg, preferably at least 0.01 mg, in particular at least 0.1 mg, to a maximum of 1 g, preferably to 100 mg, in particular to a maximum of 10 mg per kg of body weight.

Explanation of the abbreviations used in the text
DMSO Dimethyl sulfoxide
NBS N-bromosuccinimide
M mole

EXAMPLE 1

6-Cyano-4-(N-Ethylsulfonyl-N-Methylamino)-7-Fluoro-2,2-Dimethyl-3-Chromanol

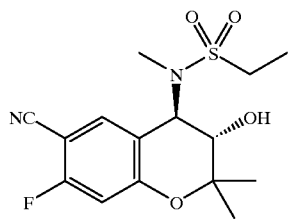

a) 10 g (0.072 M) of 2-fluoro-4-hydroxybenzonitrile, 0.072 M of 3-chloro-3,3-dimethylpropyn and 15 g (equivalent to 16.3 ml or 0.036 M) of benzyltrimethylammonium hydroxide (40% strength in methanol) are suspended in 80 ml of methylene chloride, a solution of 4.32 g (0.108 M) of NaOH in 80 ml of water is added, and the mixture is stirred at room temperature for 3 days. The phases are separated, and the aqueous phase is extracted several times with methylene chloride. The organic solution is washed with 10% strength NaOH and then with water and the organic solvent is distilled off under reduced pressure. 4-(1,1-Dimethyl-2-propynyloxy)-2-fluorobenzonitrile is obtained as a red-colored oily product.

b) 9.6 g (0.047 M) of 4-(1,1-dimethyl-2-propynyloxy)-2-fluorobenzonitrile are heated in about 30 ml of 1,2-dichlorobenzene at 170° C. under argon with magnetic stirring for 6 hours. The solvent is distilled off, and the amorphous residue is chromatographed on silica gel with a mixture of 1 part of ethyl acetate and 3 parts of toluene as eluent. 6-Cyano-7-fluoro-2,2-dimethyl-3,4-chromene is obtained as viscous oil.

c) 2.03 g (0.01 M) of 6-cyano-7-fluoro-2,2-dimethyl-3,4-chromene are dissolved in a mixture of 8 ml of DMSO and 0.3 ml of water and, with efficient external cooling, 3.54 g (0.02 M) of N-bromosuccinimide are added in portions so that the temperature is to be kept where possible below 20° C., but in any event below 30° C. Stirring at 15–20° C. for a further 3 hours is followed by pouring into a suspension of ice and water, extraction of the aqueous phase with ethyl acetate and drying over anhydrous sodium sulfate. After the solvent has been distilled off, the amorphous residue is chromatographed on silica gel with a toluene/ethyl acetate mixture (3:1) as eluent. Crystallization from n-heptane and a little diisopropyl ether affords trans-4-bromo-6-cyano-7-fluoro-3-hydroxy-2,2-dimethylchroman as a brownish-colored crystalline solid, melting point 75–82° C.

d) 1.05 g (0.026 M) of ground sodium hydroxide are added to a solution of 1.2 g (0.0039 M) of trans-4-bromo-6-cyano-7-fluoro-3-hydroxy-2,2-dimethylchroman in 40 ml of anhydrous tetrahydrofuran, and the suspension is stirred at room temperature for 3 hours. The precipitate is filtered off, and the organic phase is washed with an aqueous sodium chloride solution. Evaporation of the organic solvent in vacuo results in 6-cyano-7-fluoro-2,2-dimethyl-3,4-epoxychroman as an amorphous residue which crystallizes from n-heptane, melting point 68–70° C.

e) 0.78 g (0.0063 M) of N-methylethylsulfonamide are dissolved in 5 ml of anhydrous DMSO and added dropwise under argon to a suspension of 0.045 g (0.0015 M) of sodium hydride (60% suspension in oil), the reaction taking place with formation of hydrogen. To the mixture obtained in this way is added dropwise a solution of 1.17 g (0.005 M) of 6-cyano-7-fluoro-2,2-dimethyl-3,4-epoxychroman in 10 ml of DMSO, and the reaction mixture is stirred at 60° C. for 6 to 10 hours and at room temperature for a further 14 hours. Addition of water is followed by stirring at room temperature for several hours and filtration of the 6-cyano-4-(N-ethylsulfonyl-N-methylamino)-7-fluoro-2,2-dimethyl-3-chromanol as colorless solid, melting point 179–182° C.

EXAMPLE 2

7-Chloro-6-Cyano-4-(N-Ethylsulfonyl-N-Methylamino)-2,2-Dimethyl-3-Chromanol

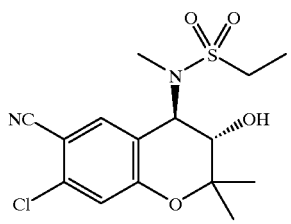

a) 5.1 g (0.026 M) of 4-acetoxy-2-chlorobenzonitrile (prepared by heating 2-chloro-4-hydroxybenzonitrile in acetic anhydride, melting point 76–78° C.) are mixed with 10.43 g (0.078 M) of anhydrous aluminum chloride as Friedel-Crafts catalyst, and the mixture of the two solids is heated with mechanical stirring to 120–130° C. over 60–90 minutes. The amorphous residue is cautiously decomposed with water, and the aqueous suspension is stirred for 1 hour. The 4-chloro-5-cyano-2-hydroxyacetophenone is filtered off and crystallized from a mixture of ethyl acetate and diisopropyl ether, yielding a colorless crystals, melting point 183–187° C.

b) a mixture of 2.5 g (0.0127 M) of 4-chloro-5-cyano-2-hydroxy-acetophenone in 100 ml of toluene is mixed with 1.8 g (0.0317 M) of acetone and 0.23 g (0.033 M) of pyrrolidine and boiled under reflux with a water trap for 3 hours. Addition of a further 2.3 ml of acetone and 0.1 ml of pyrrolidine is followed by boiling with a water trap for 6 hours. The solvent is distilled off, and the residue is mixed with water and extracted with ethyl acetate. The organic phase is washed with 2 N HCl and water and then the solvent is distilled off and the amorphous 7-chloro-6-cyano-2,2-dimethyl-4-chromanone is induced to crystallize with diisopropyl ether, melting point 88–95° C.

c) 1.32 g (0.035 M) of sodium borohydride are introduced in portions into a mixture of 5.89 g (0.025 M) of 7-chloro-6-cyano-2,2-dimethylchromanone in 120 ml of ethanol with magnetic stirring. The solution is stirred at room temperature for 4 hours, the solvent is distilled off, water is added to the residue, and the pH is adjusted to 6–7 with 2 N HCl. The suspension is stirred at room temperature for about 2 hours, and the crystalline 7-chloro-6-cyano-2,2-dimethyl-4-chromanol is filtered off, melting point 88–92° C.

d) a mixture of 5.1 g (0.021 M) of 7-chloro-6-cyano-2,2-dimethyl-4-chromanol, 250 mg of p-toluenesulfonic acid and 200 ml of toluene is boiled with a water trap and reflux condenser for 7 hours, the solvent is distilled off, and the 7-chloro-6-cyano-2,2-dimethyl-3,4-chromene is induced to crystallize with water, melting point 74–80° C.

e) trans-4-bromo-6-cyano-7-chloro-3-hydroxy-2,2-dimethylchroman is obtained in analogy to the method indicated under 1 c) by reacting 7-chloro-6-cyano-2,2-dimethyl-3,4-chromene with N-bromosuccinimide and water. Pale yellow crystals are obtained from diisopropyl ether, melting point: 152–155° C.

f) 6-cyano-7-chloro-2,2-dimethyl-3,4-epoxychroman is obtained in analogy to the method indicated in Example 1 d) by reacting trans-4-bromo-6-cyano-7-chloro-3-hydroxy-2,2-dimethylchroman with NaOH in THF, yielding a crystalline solid, melting point 129–132° C.

g) 7-chloro-6-cyano-4-(N-ethylsulfonyl-N-methylamino)-2,2-dimethyl-3-chromanol is obtained in analogy to the method indicated in Example 1 e) from 6-cyano-7-chloro-2,2-dimethyl-3,4-epoxychroman and N-methylethylsulfonamide with NaH in DMSO. Colorless crystals are obtained from a mixture of diisopropyl ether and a little ethyl acetate, melting point 179–182° C.

EXAMPLE 3
3-Acetoxy-7-Chloro-6-Cyano-4-(N-Ethylsulfonyl-N-Methylamino)-2,2-Dimethylchroman

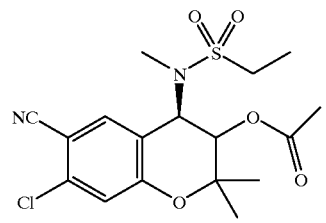

1.44 g (0.014 M) of acetic anhydride are added dropwise to a solution of 0.6 g (0.0016 M) of 6-cyano-4-(N-ethylsulfonyl-N-methylamino)-7-fluoro-2,2-dimethyl-3-chromanol in 8 ml of anhydrous pyridine while cooling in ice, and the mixture is allowed to reach room temperature after removing the ice bath. The mixture is stirred at room temperature for 2 days, the solvent is distilled off, and the residue is induced to crystallize with water, yielding a colorless crystalline product, melting point 157–160° C.

EXAMPLE 4
7-Chloro-4-(N-Ethylsulfonyl-N-Methylamino)-6-Fluoro-2,2-Dimethyl-3-Chromanol

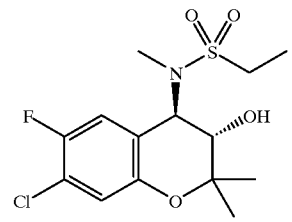

a) 4-chloro-5-fluoro-2-hydroxyacetophenone is obtained in analogy to the method indicated in Example 2a) from 4-acetoxy-2-chlorofluorobenzene (prepared by heating 3-chloro-4-fluorophenol in acetic anhydride, melting point 39–44° C.) by heating with anhydrous aluminum chloride as Friedel-Crafts catalyst. Crystalline substance, melting point 74–75° C., is obtained by crystallization from a mixture of n-heptane and diisopropyl ether.

b) 7-chloro-6-fluoro-2,2-dimethyl-4-chromanone is obtained in analogy to the method indicated in Example 2b) from 4-chloro-5-fluoro-2-hydroxyacetophenone and acetone in the presence of pyrrolidine as catalyst, producing a partially crystallized oil.

c) 7-chloro-6-fluoro-2,2-dimethyl-4-chromanol is obtained in analogy to the method indicated in Example 2c) by reducing 7-chloro-6-fluoro-2,2-dimethyl-4-chromanone with sodium borohydride, yielding a pale oily product.

d) 7-chloro-6-fluoro-2H-2,2-dimethyl-4-chromene is obtained in analogy to the method indicated in Example 2d) by acid-catalyzed water elimination from 7-chloro-6-fluoro-2,2-dimethyl-4-chromanol with p-toluenesulfonic acid, yielding a brown oily product.

e) trans-4-bromo-7-chloro-6-fluoro-3-hydroxy-2,2-dimethylchroman is obtained in analogy to the method indicated under 1 c) by reacting 7-chloro-6-fluoro-2,2-dimethyl-4-chromene with N-bromosuccinimide and water, yielding a pale yellow crystals, melting point: 97–99° C.

f) 7-chloro-6-fluoro-2,2-dimethyl-3,4-epoxychroman is obtained in analogy to the method indicated in Example 1d) by reacting trans-4-bromo-7-chloro-6-fluoro-3-hydroxy-2,2-dimethylchroman with NaOH in THF, yielding an oily product.

g) 7-chloro-4-(N-ethylsulfonyl-N-methylamino)-6-fluoro-2,2-dimethyl-3-chromanol is obtained in analogy to the method indicated in Example 1e) from 7-chloro-6-fluoro-2,2-dimethyl-3,4-epoxychroman and N-methylethylsulfonamide with NaH in DMSO, yielding a pale beige crystalline compound, melting point 188–190° C.

EXAMPLE 5
4-(N-Butyl-N-Ethylsulfonylamino)-7-Chloro-6-Fluoro-2,2-Dimethyl-3-Chromanol

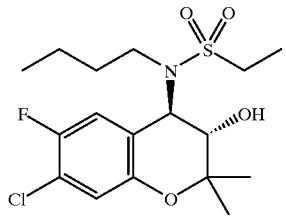

is obtained in analogy to the method indicated in Example 1e) from 7-chloro-6-fluoro-2,2-dimethyl-3,4-epoxychroman and N-butylethylsulfonamide with NaH in DMSO.

EXAMPLE 6
3-Acetoxy-7-Chloro-4-(N-Ethylsulfonyl-N-Methylamino)-6-Fluoro-2,2-Dimethylchroman

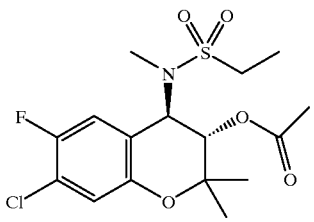

is obtained in analogy to the method indicated in Example 3 from 7-chloro-4-(N-ethylsulfonyl-N-methylamino)-6-fluoro-2,2-dimethyl-3-chromanol and acetic anhydride in pyridine, yielding a colorless crystalline substance, melting point 143–144° C.

EXAMPLE 7
7-Chloro-4-(N-Ethylsulfonyl-N-Methylamino)-6-Fluoro-2,2-Dimethyl-2H-Chromene

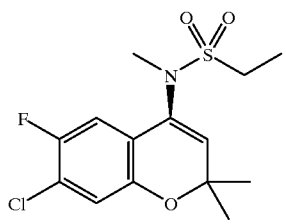

A mixture of 0.6 g of 3-acetoxy-7-chloro-4-(N-ethylsulfonyl-N-methylamino)-6-fluoro-2,2-dimethylchroman, 1.2 ml of DBU and 15 ml of toluene is heated with a reflux condenser for 2 hours, and the solvent is distilled off. The residue is dissolved in ethyl acetate, and then the organic phase is washed with 2 N hydrochloric acid, with water and then with saturated sodium bicarbonate solution and the solvent is distilled off. The viscous oil is induced to crystallize with n-heptane, melting point 83–84° C.

EXAMPLE 8
6,8-Dichloro-4-(N-Ethylsulfonyl-N-Methylamino)-2,2-Dimethyl-3-Chromanol

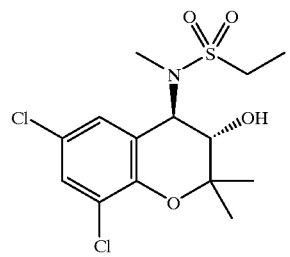

a) 6,8-dichloro-2,2-dimethyl-4-chromanone is obtained in analogy to the method indicated in Example 2b) from 3,6-dichloro-2-hydroxyacetophenone and acetone with catalysis by pyrrolidine, yielding a dark-colored viscous oil.
b) 6,8-dichloro-2,2-dimethyl-4-chromanol is obtained in analogy to the method indicated in Example 2c) by reducing 6,8-dichloro-2,2-dimethyl-4-chromanone with sodium borohydride, yielding a brown oily product.
c) 6,8-dichloro-2H-2,2-dimethyl-3-chromene is obtained in analogy to the method indicated in Example 2d) by acid-catalyzed water elimination from 6,8-dichloro-2,2-dimethyl-4-chromanol with p-toluenesulfonic acid.
d) trans-4-bromo-6,8-dichloro-3-hydroxy-2,2-dimethylchroman is obtained in analogy to the method indicated under 1c) by reacting 6,8-dichloro-2H-2,2-dimethyl-3-chromene with N-bromosuccinimide and water, yielding a beige-colored crystalline substance, melting point: 46° C.
e) 6,8-dichloro-2,2-dimethyl-3,4-epoxychroman is obtained in analogy to the method indicated in Example 1d) by reacting trans-4-bromo-6,8-dichloro-3-hydroxy-2,2-dimethylchroman with NaOH in THF, yielding a dark oily product.
f) 6,8-dichloro-4-(N-ethylsulfonyl-N-methylamino)-2,2-dimethyl-3-chromanol is obtained in analogy to the method indicated in Example 1e) from 6,8-dichloro-2,2-dimethyl-3,4-epoxychroman and N-methylethylsulfonamide with NaH in DMSO, yielding an oily product.

EXAMPLE 9
3-Acetoxy-6,8-Dichloro-4-(N-Ethylsulfonyl-N-Methylamino)-2,2-Dimethylchroman

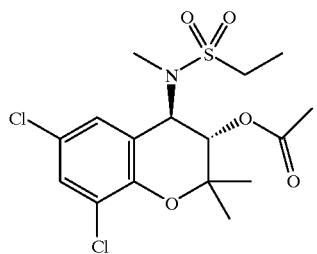

is obtained in analogy to the method indicated in Example 3 from 6,8-dichloro-4-(N-ethylsulfonyl-N-methylamino)-2,2-dimethyl-3-chromanol and acetic anhydride in pyridine, yielding a colorless crystalline substance, melting point 136–137° C.

EXAMPLE 10
4-(N-Butyl-N-ethylsulfonylamino)-6,8-dichloro-2,2-dimethyl-3-chromanol

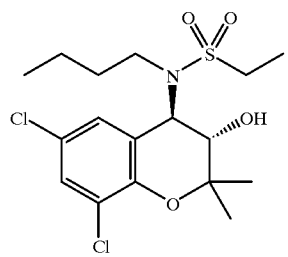

is obtained in analogy to the method indicated in Example 1e) from 6,8-dichloro-2,2-dimethyl-3,4-epoxychroman and N-butylethylsulfonamide with NaH in DMSO, yielding an oily product.

What is claimed:

1. A chroman derivative of formula I:

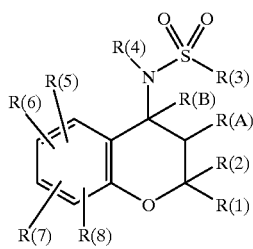

or a physiologically tolerated salt thereof in which:

R(1) and R(2)
are, independently of one another, hydrogen, $CF_3$, $C_2F_5$, $C_3F_7$, alkyl having 1, 2, 3, 4, 5 or 6 carbon atoms or phenyl,
which is unsubstituted or substituted by 1 or 2 substituents selected from F, Cl, Br, I, $CF_3$, methyl, methoxy, sulfarnoyl or methylsulfonyl;
or
R(1) and R(2)
together are an alkylene chain having 2, 3, 4, 5, 6, 7, 8, 9 or 10 carbon atoms;
R(A) is hydroxyl, alkanoyloxy having 1, 2, 3, 4, 5 or 6 carbon atoms or alkylsulfonyloxy having 1, 2, 3, 4, 5 or 6 carbon atoms;
R(B) is hydrogen;
or
R(A) and R(B)
together are a bond;
R(3) is R(9)—$C_nH_{2n}$(NR(11))$_m$—;
R(9) is hydrogen or cycloalkyl having 3, 4, 5, 6, 7 or 8 carbon atoms;
n is zero, 1, 2, 3, 4, 5, 6, 7, 8, 9 or 10;
m is zero or 1;
R(11) is hydrogen or alkyl having 1, 2, 3, 4, 5 or 6 carbon atoms;
or
R(11) and R(9)
together are an alkylene group having 1, 2, 3, 4, 5, 6, 7 or 8 carbon atoms;
wherein one $CH_2$ group in the $C_nH_{2n}$ group is optionally replaced by —O—, —$SO_{zero, 1\ or\ 2}$— or —NR(10);
R(10) is hydrogen, methyl or ethyl;
R(4) is R(12)—$C_rH_{2r}$;

R(12) is hydrogen, cycloalkyl having 3, 4, 5, 6, 7 or 8 carbon atoms, piperidyl, 1-pyrrolidinyl, N-morpholino, N-methylpiperazino, $CF_3$, $C_2F_5$, $C_3F_7$, pyridyl, thienyl, imidazolyl or phenyl,
where pyridyl, thienyl, imidazolyl or phenyl are unsubstituted or substituted by 1 or 2 substituents selected from F, Cl, Br, I, $CF_3$, methyl, methoxy, sulfamoyl, methylsulfonyl or methylsulfonylamino;
r is zero, 1, 2, 3, 4, 5, 6, 7, 8, 9, 10, 11, 12, 13, 14, 15, 16, 17, 18, 19 or 20;
wherein one $CH_2$ group in the $C_rH_{2r}$ group is optionally replaced by —O—, —CH=CH—, —C≡C—, —CO—, —CO—O—, —$SO_{zero, 1\ or\ 2}$— or —NR(10)—;
R(5), R(6), R(7) and R(8)
each independently represent hydrogen, F, Cl, Br, I, alkyl having 1, 2, 3, 4, 5 or 6 carbon atoms, cycloalkyl having 3, 4, 5, 6, 7 or 8 carbon atoms, —CN, —$CF_3$, —$C_2F_5$, —$C_3F_7$, —$N_3$, —$NO_2$, —CONR(13)R(14), —COOR(15), R(16)—$C_sH_{2s}$—Y— or phenyl,
which is unsubstituted or substituted by 1 or 2 substituents selected from F, Cl, Br, I, $CF_3$, methyl, methoxy, sulfamoyl or methylsulfonyl;
R(13) and R(14)
each independently represent hydrogen or alkyl having 1, 2 or 3 carbon atoms;
R(15) is hydrogen, methyl, ethyl, phenyl or —$C_uH_{2u}$—NR(13)R(14);
u is 2 or 3;
R(16) is hydrogen, cycloalkyl having 3, 4, 5, 6, 7 or 8 carbon atoms, —COOR(15), thienyl, imidazolyl, pyridyl, quinolyl, isoquinolyl, piperidyl, 1-pyrrolidinyl, N-morpholino, N-methylpiperazino, $CF_3$, $C_2F_5$, $C_3F_7$ or phenyl,
which is unsubstituted or substituted by 1 or 2 substituents selected from F, Cl, Br, I, $CF_3$, methyl, methoxy, sulfamoyl or methylsulfonyl;
s is zero, 1, 2, 3, 4, 5 or 6;
Y is —S—, —SO—, —$SO_2$—, —CO—, —$SO_2$—NR(10)—, —O—, —NR(10)— or —CO—NR(10);
but with the condition that two of the substituents R(5), R(6), R(7) and R(8) are not hydrogen.

2. A compound according to claim 1, in which:

R(1) and R(2)
each independently represent hydrogen, alkyl having 1, 2 or 3 carbon atoms or phenyl,
which is unsubstituted or substituted by 1 or 2 substituents selected from F, Cl, Br, I, $CF_3$, methyl, methoxy, sulfamoyl or methylsulfonyl;
or
R(1) and R(2)
together are an alkylene chain having 4 or 5 carbon atoms;
R(A) is hydroxyl or acetoxy;
R(B) is hydrogen;
or
R(A) and R(B)
together are a bond;
R(3) is R(9)—$C_nH_{2n}$(NR(11))$_m$—;
R(9) is hydrogen;
n is zero, 1, 2, 3, 4, 5 or 6;
m is zero or 1;
R(11) is hydrogen or alkyl having 1, 2, 3 or 4 carbon atoms;
R(10) is hydrogen, methyl or ethyl;

R(4) is R(12)—$C_rH_{2r}$;
  R(12) is hydrogen, cycloalkyl having 3, 4, 5, 6, 7 or 8 carbon atoms, $CF_3$, pyridyl or phenyl,
    where pyridyl and phenyl are unsubstituted or substituted by 1 or 2 substituents selected from F, Cl, $CF_3$, sulfamoyl or methylsulfonyl;
  r is zero, 1, 2, 3, 4, 5, 6, 7, 8, 9 or 10;
  wherein one $CH_2$ group in the $C_rH_{2r}$ group is optionally replaced by —O—, —CO—,
R(5), R(6), R(7) and R(8)
  each independently represent hydrogen, F, Cl, Br, alkyl having 1, 2, 3 or 4 carbon atoms, —CN, —$CF_3$, —$NO_2$, —CONR(13)R(14), —COOR(15), R(16)—$C_sH_{2s}$—Y— or phenyl,
    which is unsubstituted or substituted by 1 or 2 substituents selected from F, Cl, or $CF_3$;
  R(13) and R(14)
    each independently represent hydrogen or alkyl having 1, 2 or 3 carbon atoms;
  R(15) is methyl, ethyl, phenyl or —$C_uH_{2u}$—NR(13)R(14);
    u is 2 or 3;
  R(16) is hydrogen, cycloalkyl having 5 or 6 carbon atoms, $CF_3$, $C_2F_5$, $C_3F_7$ or phenyl,
    which is unsubstituted or substituted by 1 or 2 substituents selected from F, Cl, Br, $CF_3$, methyl, methoxy, sulfamoyl or methylsulfonyl;
  s is zero, 1, 2, 3 or 4;
  Y is —S—, —SO—, —$SO_2$—, —CO—, —$SO_2$—NR(10)—, —O—, —NR(10)— or —CO—NR(10);
but with the condition that two of the substituents R(5), R(6), R(7) and R(8) are not hydrogen.

3. A compound according to claim 1, in which
R(1) and R(2)
  each independently represent alkyl having 1, 2 or 3 carbon atoms;
or
R(1) and R(2)
  together are an alkylene chain having 4 or 5 carbon atoms;
R(A) is hydroxyl;
R(B) is hydrogen;
or
R(A) and R(B)
  together are a bond;
R(3) is alkyl having 1, 2 or 3 carbon atoms, dimethylamino or diethylamino;
R(4) is R(12)—$C_rH_{2r}$;
  R(12) is hydrogen, cycloalkyl having 5 or 6 carbon atoms or $CF_3$;
  r is zero, 1, 2, 3, 4, 5, 6, 7 or 8;
  wherein one $CH_2$ group in the $C_rH_{2r}$ group is optionally replaced by —O—, —CO—, —CO—O—, —$SO_{zero, 1 \text{ or } 2}$—;
R(5), R(6), R(7) and R(8)
  each independently represent hydrogen, F, Cl, Br, alkyl having 1 or 2 carbon atoms, —CN, —$NO_2$, —COOR(15), R(16)—$C_sH_{2s}$—Y— or phenyl, which is unsubstituted or substituted by 1 or 2 substituents selected from F or Cl;
  R(15) is methyl, ethyl, phenyl or —$C_uH_{2u}$—NR(13)R(14);
    u is 2 or 3;
  R(13) and R(14)
    each independently represent hydrogen or alkyl having 1, 2 or 3 carbon atoms;
  R(16) is hydrogen, $CF_3$ or phenyl,
  s is zero, 1, 2, 3 or 4;
  Y is —S—, —SO—, —$SO_2$—, —CO—, —$SO_2$—NR(10)—, —O—, —NR(10)— or —CO—NR(10);
    R(10) is hydrogen or methyl;
but with the condition that two of the substituents R(5), R(6), R(7) and R(8) are not hydrogen.

4. A method of treating or preventing illnesses associated with the $K^+$ channel that is opened by cyclic adenosine monophosphate (cAMP), comprising administering to a host in need thereof an effective amount of a compound according to claim 1 or a physiologically tolerated salt thereof.

5. A method of inhibiting gastric acid secretion, comprising administering to a host in need thereof an effective amount of a compound according to claim 1 or a physiologically tolerated salt thereof.

6. A method of treating or preventing ulcers of the stomach, comprising administering to a host in need thereof an effective amount of a compound according to claim 1 or a physiologically tolerated salt thereof.

7. A method of treating or preventing ulcers of the intestinal region, comprising administering to a host in need thereof an effective amount of a compound according to claim 1 or a physiologically tolerated salt thereof.

8. A method according to claim 7, where the ulcer is of the duodenum.

9. A method of treating or preventing reflux esophagitis, comprising administering to a host in need thereof an effective amount of a compound according to claim 1 or a physiologically tolerated salt thereof.

10. A method of treating or preventing diarrheal disorders, comprising administering to a host in need thereof an effective amount of a compound according to claim 1 or a physiologically tolerated salt thereof.

11. A method of treating or preventing arrhythmias, comprising administering to a host in need thereof an effective amount of a compound according to claim 1 or a physiologically tolerated salt thereof.

12. A method according to claim 11, wherein the arrhythmia is ventricular or supraventricular.

13. A method according to claim 11, wherein the arrhythmia is atrial.

14. A method according to claim 11, wherein the arrhythmia is a reentry arrhythmia.

15. A method of treating or preventing sudden heart death as a result of ventricular fibrillation, comprising administering to a host in need thereof an effective amount of a compound according to claim 1 or a physiologically tolerated salt thereof.

16. A pharmaceutical composition, comprising an amount of a compound according to claim 1 or a physiologically tolerated salt thereof and a pharmaceutically acceptable carrier.

* * * * *

UNITED STATES PATENT AND TRADEMARK OFFICE
CERTIFICATE OF CORRECTION

PATENT NO.: 6,071,953
DATED: June 6, 2000
INVENTORS: Hans Jochen LANG et al.

It is certified that an error appears in the above-identified patent and that said Letters Patent is hereby corrected as shown below:

Claim 1, Column 19, line 39, "sulfarnoyl" should read --sulfamoyl--.

Claim 1, Column 20, line 40, "-SO$_2$-," should read -- SO$_2$ -,--.

Claim 2, Column 21, line 9, after "-CO-,", insert--- CO-O-, -SO$_{zero, 1\, or\, 2}$ ---.

Claim 2, Column 21, line 30, "-SO$_2$-," should read -- SO$_2$ -,--.

Claim 3, Column 21, lines 55-56, "-SO$_{zero, 1\, or\, 2}$-," should read ---SO$_{zero, 1\, or\, 2}$ -,--.

Signed and Sealed this

First Day of May, 2001

Attest:

NICHOLAS P. GODICI

Attesting Officer

Acting Director of the United States Patent and Trademark Office